United States Patent [19]

Richardson et al.

[11] 4,214,074

[45] Jul. 22, 1980

[54] HYDROXYALKYL DERIVATIVES OF AMINOGLYCOSIDE ANTIBIOTICS

[75] Inventors: Kenneth Richardson; Rhona M. Plews, both of Canterbury; James R. Wright, Deal, all of England

[73] Assignee: Pfizer Inc., New York, N.Y.

[21] Appl. No.: 958,409

[22] Filed: Nov. 7, 1978

Related U.S. Application Data

[63] Continuation-in-part of Ser. No. 859,376, Dec. 12, 1977, abandoned, which is a continuation-in-part of Ser. No. 804,322, Jun. 7, 1977, abandoned.

[30] Foreign Application Priority Data

| Jun. 16, 1976 [GB] | United Kingdom | 24989/76 |
| Sep. 28, 1976 [GB] | United Kingdom | 40145/76 |
| Dec. 8, 1976 [GB] | United Kingdom | 51294/76 |

[51] Int. Cl.² .................. A61K 31/71; C07H 15/22
[52] U.S. Cl. ............................ 536/10; 435/80; 424/180; 536/17 R
[58] Field of Search ........................ 536/10, 17

[56] References Cited

U.S. PATENT DOCUMENTS

| 4,000,261 | 12/1976 | Daniels | 536/10 |
| 4,000,262 | 12/1976 | Daniels | 536/10 |
| 4,002,742 | 1/1977 | Wright et al. | 536/17 |
| 4,062,947 | 12/1977 | Wright et al. | 536/10 |
| 4,085,208 | 4/1978 | Mallams et al. | 536/17 |

FOREIGN PATENT DOCUMENTS

1033394 6/1966 United Kingdom ............... 536/17

*Primary Examiner*—Johnnie R. Brown
*Attorney, Agent, or Firm*—Connolly and Hutz

[57] ABSTRACT

Certain 2-deoxystreptamine aminoglycoside antibiotics, substituted on the 1-amino group by an alkyl group bearing one or more hydroxy groups, are useful antibacterial agents. The 2-deoxystreptamine aminoglycoside compounds which are substituted in this manner include the kanamycins, the gentamicins, tobramycin, ribostamycin, the neomycins, and 6'-N-alkyl derivatives thereof.

19 Claims, No Drawings

HYDROXYALKYL DERIVATIVES OF AMINOGLYCOSIDE ANTIBIOTICS

CROSS-REFERENCE TO RELATED APPLICATIONS

This application is a continuation-in-part of application Ser. No. 859,376, filed Dec. 12, 1977 and now abandoned, which is a continuation-in-part of application Ser. No. 804,322 filed June 7, 1977 and now abandoned.

BACKGROUND OF THE INVENTION

This invention relates to antibacterial agents and is particularly concerned with novel, semi-synthetic, 2-deoxystreptamine aminoglycosides and with methods for their preparation. Known 2-deoxystreptamine aminoglycosides include such valuable chemotherapeutic agents as the kanamycins, gentamicin, tobramycin, ribostamycin and the neomycins.

The novel antibacterial agents of this invention are a series of 2-deoxystreptamine aminoglycosides in which the amino group on the 1-position is substituted with an alkyl group bearing one or more hydroxyl groups on carbon atoms other than that linked to the amino group. Such compounds are effective in treating a variety of gram-positive and gram-negative bacterial infections, including urinary tract infections, in animals, including humans, and they possess advantages in use over 2-deoxystreptamine aminoglycosides having an unsubstituted amino group in the 1-position of the 2-deoxystreptamine ring. In particular, the compounds of the invention have been found to posses properties associated with a lower toxicity than many known aminoglycosides.

Belgian Pat. No. 818,431 and U.S. Pat. No. 4,002,742 disclose derivatives of gentamicins A, $B_1$, $C_1$, $C_{1a}$, $C_2$, $C_{2a}$, $C_{2\beta}$ and $X_2$; sisomicin, verdamicin; tobramycin; antibiotics G-418, 66-40B, 66-40D, J1-20A, J1-20B and G-52; and mutamicins 1, 2, 4, 5 and 6, substituted on the 1-amino function. Among the broad terms mentioned for the 1-amino substituent is "hydroxyalkyl". However, Belgian Pat. No. 818,431 and U.S. Pat. No. 4,002,742 do not disclose any compounds having more than one hydroxy in the alkyl group on the 1-amino function, and they do not disclose any compounds possessing the specific monohydroxyalkyl groups of the present invention. In particular, Belgian Pat. No. 818,431 and U.S. Pat. No. 4,002,742 do not disclose any compounds with monohydroxyalkyl groups in which there is branching at the carbon atom adjacent to the nitrogen atom of the 1-amino function. Additionally, Belgian Pat. No. 818,431 and U.S. Pat. No. 4,002,742 do not disclose any kanamycin derivatives.

Belgian Pat. No. 835,898 and U.S. Pat. No. 4,000,261 disclose 5-epi aminoglycoside derivatives, including kanamycins A and B and tobramycin, having a hydroxyalkyl group on the 1-amino function. However, there is no disclosure of alkyl groups substituted with more than one hydroxy group, and there is no specific disclosure of hydroxyalkyl groups which have branching at the carbon atom adjacent to the nitrogen atom of the 1-amino function.

U.S. Pat. No. 4,000,262 discloses 1-N-hydroxyalkyl derivatives of 5-epi-azido-5-deoxy-kanamycins A and B, 5-epi-amino-5-deoxy-kanamycins A and B, 5-epi-azido-5-deoxy-tobramycin and 5-epi-amino-5-deoxy-tobramycin.

U.S. Pat. No. 4,085,208 discloses 1-N-hydroxyalkyl derivatives of 1-epi-kanamycins A and B and 1-epi-tobramycin.

Belgian Pat. No. 834,864 discloses derivatives of 2-deoxystreptamine aminoglycoside antibiotics which have an ω-amino-2-hydroxyalkyl group on the 1-amino function.

U.S. Pat. Nos. 3,282,783 and 3,350,387 and British Pat. No. 1,033,394 disclose a broad genus of N-alkylated derivatives of aminoglycoside antibiotics, including derivatives of the kanamycins and tobramycin, in which said N-alkyl groups can contain hydroxy groups. However, these N-alkylated derivatives are reported to be substantially devoid of antibiotic properties by virtue of this alkylation.

SUMMARY OF THE INVENTION

According to the invention there are provided novel 2-deoxystreptamine aminoglycosides of the general formula

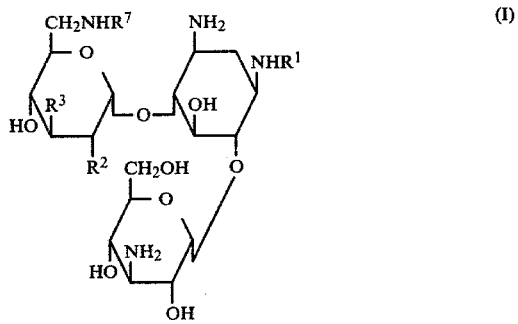

and the pharmaceutically-acceptable acid-addition salts thereof; wherein $R^2$ is selected from the group consisting of hydroxy and amino;

$R^3$ is selected from the group consisting of hydrogen and hydroxy;

$R^7$ is selected from the group consisting of hydrogen and alkyl having from 1 to 4 carbon atoms; and $R^1$ is selected from the group consisting of

and

wherein $R^8$ is alkyl having from 2 to 5 carbon atoms at least 2 of which bear one hydroxy group;

$R^9$ is alkyl having from 1 to 5 carbon atoms at least one of which bears one hydroxy group; and $R^{10}$ is selected from the group consisting of alkyl having from 1 to 5 carbon atoms, and alkyl having from 1 to 5 carbon atoms at least one of which bears one hydroxy group;

provided that when $R^2$ is amino and $R^3$ is hydrogen, $R^{10}$ is alkyl having from 1 to 5 carbon atoms at least one of which bears one hydroxy group.

A preferred group of compounds according to the invention are the compounds of the formula I, wherein $R^2$ is selected from the group consisting of hydroxy and amino, $R^3$ is hydroxy, $R^7$ is hydrogen, and $R^1$ is $CH_2R^8$, wherein $R^8$ is a straight-chain alkyl group having from 2 to 5 carbon atoms, each of which bears one hydroxy group. A particularly preferred group for $R^8$ is a 1,2-dihydroxyethyl group.

A second preferred group of compounds according to the invention are the compounds of the formula I, wherein $R^2$ is selected from the group consisting of hydroxy and amino, $R^3$ is hydroxy, $R^7$ is hydrogen, and $R^1$ is

wherein $R^9$ and $R^{10}$ are each straight-chain alkyl having from one to five carbon atoms each of which bears one hydroxy group. Particularly preferred compounds of this group are those wherein $R^9$ and $R^{10}$ are each hydroxymethyl.

Particularly preferred individual compounds according to the invention are 1-N-[2,3-dihydroxypropyl]kanamycins A and B, 1-N-[1-(hydroxymethyl)-2-hydroxyethyl]kanamycins A and B, and 1-N-[1-methyl-2-hydroxyethyl]kanamycins A and B.

DETAILED DESCRIPTION OF THE INVENTION

The compounds of this invention are the compounds of formula I, and the pharmaceutically-acceptable acid-addition salts thereof, wherein $R^1$, $R^2$, $R^3$ and $R^7$ are as defined previously, provided that when $R^2$ is amino and $R^3$ is hydrogen, $R^{10}$ is alkyl having from 1 to 5 carbon atoms at least one of which bears 1 hydroxy group.

The compounds of this invention are derived from kanamycins A and B, tobramycin (nebramycin factor 6) and 3'-deoxykanamycin A, the structures of which are known. See further: The Merck Index, An Encyclopedia of Chemicals & Drugs, Eighth Edition, 1968, P. G. Stecher editor, Merck & Co., Rahway, N.J., page 597; Koch & Rhoades, *Antimicrobial Agents & Chemotherapy*, 309 (1970); Umezawa et al., *Bulletin of the Chemical Society of Japan*, 45, 2847 (1972). Therefore, at the points of attachment of the substituents to the various rings in the compound of formula I, the stereochemistries correspond to those found in the kanamycins, tobramycin and 3'-deoxykanamycin A. These stereochemistries are as shown hereinbefore in formula I.

Pharmaceutically-acceptable acid-addition salts of the compounds of the invention are those formed from acids which form non-toxic acid-addition salts containing pharmaceutically-acceptable anions, such as the hydrochloride, hydrobromide, sulphate or bisulphate, phosphate or acid phosphate, acetate, maleate, fumarate, succinate, lactate, tartrate, citrate, gluconate, saccharate, p-toluenesulphonate and carbonate salts. The salts are prepared in conventional manner, such as, for example, combining a solution containing the compound of the formula I with a solution of the appropriate acid. If the salt precipitates, it can be removed by filtration; alternatively, it can be recovered by evaporation of the solvent in vacuo.

The compounds of formula I can be prepared according to the invention by alkylation of a compound of the formula:

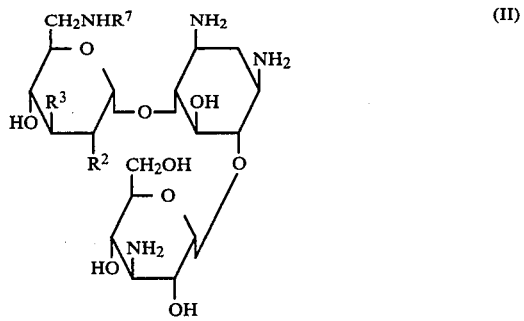

wherein $R^2$, $R^3$ and $R^7$ are as previously defined and in which one or more of the free amino groups, other than the 1-amino group, may optionally be protected; and removal of the amino protecting groups (if present) and isolation of the compound of formula (I).

The optional protection of free amino groups in the compound of formula (II) can be achieved by reaction with a reagent selective for free amino groups and easily removable therefrom subsequently by conventional techniques, for example, by hydrolysis or hydrogenolysis. Examples of suitable protecting groups are the formyl, acetyl, trifluoroacetyl, methoxycarbonyl, t-butyloxycarbonyl and benzyloxycarbonyl groups.

The alkylation can be achieved by conventional reactions, for example, by reductive alkylation using an appropriate hydroxy-substituted aldehyde or ketone or, in the case where $R^1$ is $CH_2$—$R^8$, by acylation with an appropriate hydroxy-substituted acid and reduction of the corresponding acylated derivative (e.g. with diborane). Naturally, in cases where there are free amino groups present in addition to the 1-amino group, reaction will also take place on these and it will then be necessary to separate the required 1-N-substituted derivative from the mixture of products obtained. This can be achieved by conventional techniques, for example by ion-exchange chromatography. It is, however, desirable to protect some or preferably all of the amino groups other than the 1-amino group during the alkylation reaction in order to simplify the final isolation of the required product. In this case, it will be necessary to remove the protecting groups as an extra step in the process.

Thus, in one process for the preparation of compounds of the formula (I), a selectively protected aminoglycoside derivative of the formula (II), having a free 1-amino group, is reacted with the aldehyde or ketone, the latter preferably being used in excess, and the Schiff's base initially formed in the reaction is reduced simultaneously or in a stepwise fashion to give the 1-N-substituted product. The reduction can suitably be effected using sodium borohydride or sodium cyanoborohydride as the reducing agent and is conveniently performed by adding the latter to the reaction mixture, at a pH generally between 4 and 7, enabling the reaction to be performed effectively in a single stage. Alternatively, the mixture of the aminoglycoside (II) and the aldehyde or ketone can be subjected to a conventional catalytic hydrogenation.

The reaction can conveniently be performed with the reactants dissolved in a reaction-inert solvent, e.g.

water or aqueous dioxan or aqueous methanol at a temperature between 0° C. and the reflux temperature of the solvent. The period within which the reaction goes substantially to completion naturally depends on the nature of the reactants, solvent and the temperature employed, but we have found that the reaction between the aminoglycoside of formula (II) and the hydroxy-substituted aldehyde or ketone (e.g. glyceraldehyde or dihydroxyacetone) in the presence of an excess of sodium cyanoborohydride, at a pH between 4 and 7, is generally substantially complete within 2 days when performed in aqueous methanol at a temperature of 60° C.

As a second step in the preparation, it is necessary to remove any amino protecting groups which are present in the aminoglycoside molecule. There are various conditions for completely removing amino-protecting groups which depend on the nature of the protecting group employed and the environment of the protected amine. The medium employed can be anhydrous or aqueous and in particular instances it can be acidic or basic to various strengths. A particularly preferred protecting group for the compounds of formula (II) is the formyl group. This can readily be removed by mild basic hydrolysis, for example, by treatment with dilute sodium hydroxide at room temperature for several hours, or by heating with hydrazine acetate or by mild acidic hydrolysis, for example, with 3 N hydrochloric acid at room temperature for several hours. Also suitable are the t-butyloxycarbonyl group which can be removed under acidic conditions, for example by treatment with anhydrous trifluoroacetic acid at room temperature for up to 45 minutes; the benzyloxycarbonyl group which can be removed by catalytic hydrogenolysis, e.g. by hydrogenation in aqueous acetic acid solution in the presence of palladium-on-charcoal catalyst at 30° C. and a pressure of 50 p.s.i. for several hours; and the acetyl group which is removed by heating with 3 N sodium hydroxide at 80°–90° C. for several hours. The product after removal of the protecting groups is finally worked up in a conventional manner e.g. by filtration and evaporation of the solvent. The crude product may then be purified by crystallization or by chromatography, if desired.

A particularly preferred protected aminoglycoside derivative of formula (II) for use in the process for the preparation of kanamycin A derivatives of formula (I), wherein $R^7$ is hydrogen and $R^2$ and $R^3$ are hydroxyl, is 3,3'',6'-tri-N-formyl-kanamycin A. The corresponding 2',3,3'',6'-tetra-N-formyl-kanamycin B derivative is preferred for preparation of 1-N-substituted kanamycin B derivatives of formula (I), wherein $R^2$ is amino, $R^3$ is hydroxy and $R^7$ is hydrogen. Also suitable are the selectively protected kanamycin A and B derivatives 3'',6'-di-N-acetyl-kanamycin A; 2',3'',6'-tri-N-trifluoroacetyl-kanamycin B; 3'',6'-di-N-trifluoroacetyl-kanamycin A and 3-N-benzyl-3'',6'-di-N-trifluoroacetyl-kanamycin A.

The aminoglycoside or protected aminoglycoside derivatives of formula (II) are known compounds previously described in the literature. For example, various aminoglycosides N-formylated on all but the 1-amino group, and including 3,3'',6'-tri-N-formyl-kanamycin A and 2',3,3'',6'-tetra-N-formylkanamycin B, are described in Belgian patent specification No. 817,546. Similar derivatives of other aminoglycosides can be prepared in an analogous manner. Derivatives in which the 6'-amino group is protected are well known and their preparation is described, for example, in British patent specification No. 1,401,220 and in West German patent specification Nos. 2,311,524; 2,350,169 and 2,512,587.

Hydroxy-substituted aldehydes and ketones suitable for use in the process for the preparation of compounds of formula (I) are readily available. For example, D-glyceraldehyde when used in the process gives rise to a product in which $R^1$ is (S)2,3-dihydroxypropyl. Other readily-available aldoses and deoxyaldoses can also be used in the reaction, e.g. D-erythrose, D-ribose and 2-deoxy-D-ribose. Similarly, dihydroxyacetone can be used to give the 1-N-[1-(hydroxymethyl)-2-hydroxyethyl] derivative and hydroxyacetone (acetol) to give the corresponding 1N-[1-methyl-2-hydroxyethyl]-derivative.

When the hydroxy-substituted-alkyl substituent on the 1-amino group has one or more optically active centers, each center can be in the R or S configuration, or a mixture of configurations can be present at each center.

The in vitro evaluation of compounds of the invention as antibacterial agents is performed by determining the minimum inhibitory concentration (MIC) of the test compound in a suitable medium at which growth of the particular microorganism fails to occur. In practice, agar plates, each having incorporated therein the test compound at a particular concentration, are inoculated with a standard number of cells of the test microorganisms and each plate is then incubated for 24 hours at 37° C. The plates are then observed for the presence or absence of the growth of bacteria and the appropriate MIC value noted. Microorganisms used in such tests have included strains of *Escherichia coli, Klebsiella pneumoniae, Proteus mirabilis, Pseudomonas aeruginosa, Staphylococcus aureus* and *Streptococcus faecalis.*

In vivo evaluation is carried out by administering the compounds subcutaneously to mice which are exposed to a strain of *Escherichia coli.* Each compound is administered at a series of dosage levels to groups of mice and its activity is determined as the level at which it gives 50% protection against the lethal effect of the *Escherichia coli* organisms over a period of 72 hours.

For human use, the antibacterial compounds of the invention can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. They can be injected parenterally; for example, intravenously, intramuscularly or subcutaneously. For parenteral administration, they are best used in the form of a sterile aqueous solution which can contain other solutes; for example, enough salts or glucose to make the solution isotonic.

For administration to human patients, it is expected that the daily dosage level of the antibacterial compounds of the invention will be comparable with that of aminoglycoside antibacterial agents currently in use, e.g. from 0.1 to 50 mg./kg. (in divided doses) when administered by the parenteral routes, or from 10 to 100 mg./kg. (in divided doses) when administered by the oral route. Thus, tablets or capsules of the compounds will contain from 0.1 to 1 g. of active compound for administration orally up to 4 times a day, while dosage units for parenteral administration will contain from 10 to 500 mg. of active compound. The physician in any event will determine the actual dosage which will be most suitable for an individual patient and it will vary with age, the weight and response of the particular patient. The above dosages are exemplary of the average host. There can, of course, be individual cases where higher or lower dosage ranges are merited, and such are within the scope of this invention.

The following examples and preparations are given solely for the purpose of further illustration. Thin layer chromatography was performed on silica plates using the solvent system stated. The spots were visualized after drying the plates by spraying with a 5% solution of t-butyl-hypochlorite in cyclohexane, drying the plates at 100° C. for 10 minutes in a ventilated oven, cooling and spraying with starch-potassium iodide solution. Temperatures are given in °C. "Amberlite" is a Registered Trademark, and refers to a cationic ion-exchange resin having a polystyrene matrix cross-linked with 3°–5° of divinylbenzene which has then been sulfonated. "Sephadex" is a Registered Trademark, and refers to a chemically modified, cross-linked dextran, which acts as a molecular sieve and separates materials on the basis of molecular weight, by a process known as gel filtration. "0.880 Ammonium hydroxide" refers to the concentrated ammonium hydroxide having a specific gravity of 0.880.

EXAMPLE 1

1-N-[(S)-2,3-Dihydroxypropyl]kanamycin A 3,3″,6′-Tri-N-formyl-kanamycin A (100 mg., 0.18 mmole), D-glyceraldehyde (31.6 mg., 0.35 mmole) and sodium cyanoborohydride (33 mg, 0.52 mmole) were dissolved in aqueous methanol (10 ml methanol, 2 ml water) and the pH of the solution was adjusted to 6.0 with 5 N hydrochloric acid. The solution was kept at room temperature for 40 hours. The solvent was then evaporated under reduced pressure and the residue was treated with 1 N sodium hydroxide and allowed to stand at room temperature for a further 20 hours. After concentration under reduced pressure the residue was chromatographed on a column of Amberlite CG-50 ion exchange resin ($NH_4^+$ form), eluting with a gradient of aqueous ammonium hydroxide of increasing concentration from 0 to 0.1 N, to give 1-N-[(S)-2,3-dihydroxypropyl]kanamycin A (66 mg, 67%). Rf 0.27 in 1 M aqueous sodium chloride (kanamycin A gave an Rf value of 0.21), Rf 0.70 in methanol, 0.880 ammonium hydroxide 1:2 (kanamycin A, 0.70). Found: C, 40.1; H, 7.0; N, 8.3; $C_{21}H_{42}N_4O_{13}.2H_2CO_3$ requires C, 40.5; H, 6.8; N, 8.2%.

A sample was converted to the volatile tetra-N-acetyl-nona-O-trimethylsilyl derivative by treatment with acetic anhydride in methanol at room temperature for 24 hours followed by reaction with a 2:1 mixture of hexamethyldisilazane and trimethylchlorosilane at room temperature for 24 hours. $m/e$ found 1285. $C_{56}H_{122}N_4O_{17}Si_9$ less one $C_3H_9OSi$ group requires $m/e$ 1285.

EXAMPLE 2

1-N-[(S)(R)2,3,4-Trihydroxybutyl]kanamycin A

A solution of 3,3″,6′-tri-N-formyl-kanamycin A (100 mg, 0.18 mmole), D-erythrose (107 mg, 0.90 mmole) and sodium cyanoborohydride (66 mg, 1.04 mmole) in a mixture of methanol (10 ml) and water (2 ml) at pH 6.0 was heated at 60° for 50 hours. The solution was concentrated under reduced pressure. The residue was dissolved in 10% hydrazine hydrate (12 ml), the pH of the solution was adjusted to 6.0 with glacial acetic acid and the solution was then heated under reflux for 6 hours. The solvent was evaporated under reduced pressure and the residue was chromatographed on Amberlite CG-50 as described for Example 1, followed by chromatography of the major fraction containing the product on Sephadex CM25 ($NH_4^+$ form), eluting with a gradient of ammonium hydroxide as before, to give 1-N-[(S)(R)2,3,4-trihydroxybutyl]kanamycin A (37 mg, 36%). RF 0.29 in methanol, 0.880 ammonium hydroxide 2:1 (kanamycin A, 0.32). Found: C, 41.6; H, 6.6; N, 7.9. $C_{22}H_{44}N_4O_{14}.2H_2CO_3$ requires C, 40.5; H, 6.8; N, 7.9%.

EXAMPLE 3

1-N-[(S)(S)(R)2,3,4,5-Tetrahydroxypentyl]kanamycin A

1-N-[(S)(S)(R)2,3,4,5-Tetrahydroxypentyl]kanamycin A was prepared using the method of Example 2 but starting with D-ribose. Rf 0.68 in methanol, 0.880 ammonium hydroxide 1:2 (kanamycin A, 0.70).

EXAMPLE 4

1-N-[(S)(R)3,4,5-Trihydroxypentyl]kanamycin A

1-N[(S)(R)3,4,5-trihydroxypentyl]kanamycin A was prepared using the method of Example 2 but starting with 2-deoxy-D-ribose. Rf 0.68 in methanol 0.880 ammonium hydroxide 1:2 (kanamycin A, 0.70).

EXAMPLE 5

1-N-[(S)(R)(R)(R)2,3,4,5,6-Pentahydroxyhexyl]kanamycin A

1-N-[(S)(R)(R)(R)2,3,4,5,6-pentahydroxyhexyl]kanamycin A was prepared using the method of Example 2 but starting with D-glucose. Rf 0.55 in methanol, 0.880 ammonium hydroxide 1:2 (kanamycin A, 0.71).

EXAMPLE 6

1-N-[(R)(S)(R)2,3,4,5-Tetrahydroxypentyl]kanamycin A

1-N-[(R)(S)(R)2,3,4,5-Tetrahydroxypentyl]kanamycin A was prepared using the method of Example 2 but starting with D-arabinose. Rf 0.34 in methanol, 0.880 ammonium hydroxide 1:1 (kanamycin A, 0.49).

EXAMPLE 7

1-N[(S)(R)(R)2,3,4,5-Tetrahydroxypentyl]kanamycin A

A solution of 3,3″,6′-tri-N-formyl-kanamycin A (100 mg, 0.18 mmole), D-xylose (79 mg, 0.53 mmole) and sodium cyanoborohydride (44 mg, 0.68 mmole) in water (10 ml) at pH 4.6 was heated at 90° C. for 3½ hours. The solvent was evaporated under reduced pressure and the residue was dissolved in 5 N hydrochloric acid (10 ml) and stirred at 30° C. for 16 hours. The solvent was evaporated and the residue was chromatographed on a column of Amberlite CG-50 ion-exchange resin ($NH_4^+$ form) eluting with a gradient of aqueous ammonium hydroxide of increasing concentration from 0 to 0.2 N to give 1-N-[(S)(R)(R)2,3,4,5-tetrahydroxypentyl]kanamycin A (56 mg, 51%). Rf 0.58 in methanol, 0.880 ammonium hydroxide 1:2 (kanamycin A gave an Rf value of 0.66).

EXAMPLE 8

1-N-[(R)(S)(S)2,3,4,5-Tetrahydroxypentyl]kanamycin A

1-N-[(R)(S)(S)2,3,4,5-tetrahydroxypentyl]kanamycin A was prepared using the method of Example 7 but starting with L-xylose. Rf 0.34 in methanol, 0.88 ammonium hydroxide 1:1 (kanamycin A, 0.50).

EXAMPLE 9

1-N-[(R)(R)(S)2,3,4,5-Tetrahydroxypentyl]kanamycin A

1-N-[(R)(R)(S)2,3,4,5-tetrahydroxypentyl]kanamycin A was prepared using the method of Example 7 but starting with L-ribose. Rf 0.38 in methanol, 0.88 ammonium hydroxide 1:1 (kanamycin A, 0.51). $m/e$ (field desorption) M+1 found 619. $C_{23}H_{46}N_4O_{15}$ (requires M+1=619.

EXAMPLE 10

1-N-[(R)(R)(R)2,3,4,5-Tetrahydroxypentyl]kanamycin A

1-N-[(R)(R)(R)2,3,4,5-tetrahydroxypentyl)]kanamycin A was prepared using the method of Example 7 but starting with D-lyxose. Rf 0.37 in methanol, 0.880 ammonium hydroxide 1:1 (kanamycin A, 0.48).

EXAMPLE 11

1-N-[(S)2,3-Dihydroxypropyl]kanamycin B

A solution of D-glyceraldehyde (45 mg. 0.5 mmole) in methanol (1 ml) was added to a solution of 2',3,3'',6'-tetra-N-formyl-kanamycin B (100 mg, 0.17 mmole) in methanol (5 ml) and water (1 ml). Sodium cyanoborohydride (20 mg, 0.3 mmole) was added to the stirred solution, the pH adjusted to 6.0 with 5 N hydrochloric acid and the solution stirred at room temperature overnight. The solution was evaporated to dryness under reduced pressure and the residue was taken up in 5 N hydrochloric acid and the solution allowed to stand at room temperature overnight. The pH of the solution was adjusted to 6.0 with sodium hydroxide solution and then the solution was chromatographed on Amberlite CG-50 as described for Example 1. Lyophilization of the appropriate fractions yielded 1-N-[(S)2,3-dihydroxypropyl]kanamycin B (53 mg, 56%). Rf 0.51 in 3 M aqueous sodium chloride (kanamycin B, 0.42), Rf 0.54 in methanol, 0.880 ammonium hydroxide, 1:1 (kanamycin B, 0.58). Field desorption mass spectrometry showed a strong M+1 peak at $m/e$ 558. $C_{21}H_{43}N_5O_{12}$ requires M+1=558.

Analysis: Found: C, 40.3; H, 7.25; N, 10.3 percent. $C_{21}H_{43}N_5O_{12}.2H_2CO_3$ requires: C, 40.5; H, 6.95; N, 10.3 percent.

EXAMPLE 12

1-N-[(S)(R)2,3,4-Trihydroxybutyl]kanamycin B

1-N-[(S)(R)2,3,4-Trihydroxybutyl]kanamycin B was prepared using the method of Example 11, but starting with D-erythrose. Rf 0.60 in 3 M sodium chloride (kanamycin B, 0.45).

EXAMPLE 13

1-N-[(S)(S)(R)2,3,4,5-Tetrahydroxypentyl]kanamycin B

1-N-[(S)(S)(R)2,3,4,5-Tetrahydroxypentyl]kanamycin B was prepared using the method of Example 11, but starting with D-ribose. Rf 0.3 in 2 M sodium chloride (kanamycin B, 0.2).

EXAMPLE 14

1-N-[(S)(R)3,4,5-Trihydroxypentyl]kanamycin B

1-N-[(S)(R)3,4,5-Trihydroxypentyl]kanamycin B was prepared using the method of Example 11, but starting with 2-deoxy-D-ribose. Rf 0.3 in 2 M sodium chloride (kanamycin B, 0.2).

EXAMPLE 15

1-N-[(S)(R)(R)(R)2,3,4,5,6-Pentahydroxyhexyl]kanamycin B

1-N-[(S)(R)(R)(R)2,3,4,5,6-Pentahydroxyhexyl]kanamycin B was prepared using the method of Example 11, but starting with D-glucose. Rf 0.25 in methanol, 0.880 ammonium hydroxide 1:1 (kanamycin B, 0.42).

EXAMPLE 16

1-N-[2,3-Dihydroxy-2-hydroxymethylpropyl]kanamycin B

1-N-[2,3-Dihydroxy-2-hydroxymethylpropyl]kanamycin B was prepared using the method of Example 11, but starting with DL-2-hydroxymethyl-2,3-O-isopropylidene-glyceraldehyde. Rf 0.55 in 3 M sodium chloride (kanamycin B, 0.42). m/e (field desorption) M+1 found 588. $C_{22}H_{45}N_5O_{13}$ requires M+1=588.

EXAMPLE 17

1-N-[(R)2,3-Dihydroxypropyl]kanamycin B

1-N-[(R)2,3-Dihydroxypropyl]kanamycin B was prepared using the method of Example 11 but starting with L-glyceraldehyde. It was identical by thin layer chromatography with the product of Example 11.

EXAMPLE 18

1-N-[1-(Hydroxymethyl)-2-hydroxyethyl]kanamycin A 3,3'',6'-tri-N-formyl-kanamycin A (200 mg, 0.36 mmole), dihydroxyacetone (95 mg, 1.05 mmole) and sodium cyanoborohydride (88 mg, 1.40 mmole) were dissolved in aqueous methanol (20 ml methanol, 4 ml water) and the pH of the solution was adjusted to 6.6 with 5 N hydrochloric acid. The solution was heated under reflux for 22 hours. Further dihydroxyacetone (95 mg) and sodium cyanoborohydride (88 mg) were added and the pH adjusted to 5.5. The refluxing was continued for a further 24 hours and the solvent was then evaporated under reduced pressure and the residue was treated with 10% hydrazine hydrate/acetic acid at pH 6.0 (20 ml) and heated under reflux for 6 hours. After concentration under reduced pressure the residue was chromatographed on a column of Amberlite CG-50 ion exchange resin ($NH_4^+$ form), eluting with a gradient of aqueous ammonium hydroxide of increasing concentration from 0 to 0.1 N. Fractions containing the product (as monitored by t.l.c.) were combined, evaporated and the product re-chromatographed on Sephadex CM25 (ammonium-ion form) eluting as before to give the title compound (0.11 g, 57%). Rf 0.40 in methanol, 0.880 ammonium hydroxide, 2:1 (kanamycin A, 0.30). Found: C, 40.6; H, 6.5; N, 8.4; $C_{21}H_{42}N_4O_{13}.2H_2CO_3$ requires C, 40.5; H, 6.8; N, 8.2%

Field desorption mass spectrometry showed an M+1 peak at m/e 559; $C_{21}H_{42}N_4O_{13}$ requires 559.

EXAMPLE 19

1-N-[1-(Hydroxymethyl)-2-hydroxyethyl]kanamycin B

Sodium cyanoborohydride (88 mg, 1.40 mmole) was added to a solution of 2′,3,3″,6′-tetra-N-formyl-kanamycin B (200 mg, 0.33 mmole) and dihydroxyacetone (95 mg, 1.05 mmole) in methanol (12 ml) and water (3 ml). The pH of the solution was adjusted to 4.5 with 2 N hydrochloric acid and the solution was heated under reflux for 20 hours. The solvent was evaporated under reduced pressure and the residue dissolved in water (10 ml). Hydrazine hydrate (2 ml, 60%) was added, the pH of the solution adjusted to 6 with glacial acetic acid (2 ml) and the solution heated under reflux for 6 hours and then evaporated to a gum under reduced pressure. The product was dissolved in water (8 ml), the pH adjusted to 5.5 with 0.2 N hydrochloric acid, and the solution chromatographed on a column of Amberlite CG-50 ion-exchange resin in the ammonium ion form, eluting first with water and then a gradient of aqueous ammonium hydroxide of increasing concentration to 0.25 N. Fractions containing the product (as monitored by t.l.c.) were combined, evaporated and the product re-chromatographed on a column of Sephadex CM25 (ammonium ion form) eluting as before to give the title compound (59 mg., 32%). Rf 0.55 in methanol, 0.880 ammonium hydroxide (1:1) (kanamycin B, 0.47), Rf 0.37 in 2 M sodium chloride (kanamycin B, 0.26). Found: C, 37.6; H, 6.3; N, 9.2. $C_{21}H_{43}N_5O_{12}.3H_2CO_3.H_2O$ requires C, 37.8; H, 6.8; N, 9.2%.

Field desorption mass spectrometry showed an M+1 peak at m/e 558; $C_{21}H_{43}N_5O_{12}$ requires 558.

EXAMPLE 20

1-N-[1-Methyl-2-hydroxyethyl]kanamycin B

2′,3,3″, 6′-Tetra-N-formyl-kanamycin B (200 mg, 0.36 mmole), hydroxyacetone (78 mg, 1.05 mmole) and sodium cyanoborohydride (88 mg, 1.40 mmole) were dissolved in aqueous methanol (20 ml methanol, 4 ml water) and the pH of the solution was adjusted to 6.0 with 5 N hydrochloric acid. The solution was heated under reflux for 22 hours. Further hydroxyacetone (23 mg) and sodium cyanoborohydride (30 mg) were added and the refluxing was continued for a further 24 hours. The solvent was then evaporated under reduced pressure and the residue was treated with 10% aqueous hydrazine hydrate adjusted to pH6 with glacial acetic acid (20 ml) and heated under reflux for 6 hours. After concentration under reduced pressure the residue was chromatographed on a column of Amberlite CG-50 ion exchange resin ($NH_4^+$ form), eluting with a gradient of aqueous ammonium hydroxide of increasing concentration from 0 to 0.1 N. Fractions containing the product (as monitored by t.l.c.) were combined and evaporated to give the title compound (0.11 g, 50%). Rf 0.55 in 3 M sodium chloride (kanamycin B, 0.47). Found: 39.6; H, 6.8; N, 10.5; $C_{21}H_{43}N_5O_{11}.2\frac{1}{2}H_2CO_3$ requires C, 40.5; H, 6.9; N, 10.0%. m/e (field desorption) (M+1) found 542. $C_{21}H_{43}N_5O_{11}$ requires M+1=542.

EXAMPLE 21

1-N-[1-Methyl-2-hydroxyethyl]kanamycin A

The title compound was prepared in a similar manner to that described in Example 20 but using 3,3″,6′-tri-N-formyl-kanamycin A. Rf 0.3 in methanol, chloroform, 8% ammonium hydroxide (4:1:2) (kanamycin A, 0.20).

EXAMPLE 22

1-N-[1-Methyl-2-hydroxyethyl]tobramycin

6′-N-t-Butyloxycarbonyl-tobramycin (2.0 g, 3.5 mmole), hydroxyacetone (0.78 g, 10.6 mmole) and sodium cyanoborohydride (0.89 g, 14.0 mmole) were dissolved in a mixture of methanol (150 ml) and water (30 ml) and the pH of the solution adjusted to 6.0 with 5 N hydrochloric acid. The mixture was heated under reflux for 72 hours. The solvent was removed under reduced pressure and the residue treated with trifluoroacetic acid (20 ml) stirring for 45 minutes at room temperature. The solution was again evaporated to dryness under reduced pressure, the residue in a little water, the pH adjusted to 6.0 with 3 N ammonium hydroxide and the solution was chromatographed on Amberlite CG-50 ion exchange resin ($NH_4^+$ form) eluting with a gradient of aqueous ammonium hydroxide. Fractions containing the product were combined, evaporated and the product re-chromatographed on Sephadex CM25 (ammonium ion form) eluting as before in give 1-N-[1-methyl-2-hydroxyethyl]tobramycin (8 mg, 0.4%). Rf 0.68 in 3 M sodium chloride (tobramycin 0.60). m/e (field desorption) M+1 found 526. $C_{21}H_{43}N_5O_{10}$ requires M+1=526.

EXAMPLE 23

1-N-[(S)2,3-Dihydroxypropyl]tobramycin

1-N-[(S)2,3-Dihydroxypropyl]tobramycin was prepared in a similar manner to that described in Example 22 but using D-glyceraldehyde instead of hydroxyacetone. Rf 0.55 in 3 M sodium chloride (tobramycin 0.45), Rf 0.37 in methanol, 0.880 ammonium hydroxide (2:1)(tobramycin 0.35).

EXAMPLE 24

1-N-[1-(Hydroxymethyl)-2-hydroxyethyl]kanamycin A

6′,3″-Di-N-acetylkanamycin A (500 mg, 0.88 mmole), 1,3-dihydroxyacetone (237 mg, 2.64 mmole) and sodium cyanoborohydride (181 mg, 2.64 mmole) were dissolved in aqueous methanol (45 ml methanol, 5 ml water) and the pH of the solution was adjusted to 6.0 with 2 N hydrochloric acid. The solution was allowed to stand at room temperature for 3 days. Thin layer chromatography (methanol, chloroform, 1 N ammonium hydroxide 4:2:1) showed two major components Rf 0.17, 0.22. The solution was evaporated and the products separated by ion exchange chromatography on Sephadex CM25 ammonium-ion form, eluting with a gradient of ammonium hydroxide of increasing concentration. The slower running component (Rf 0.17) which was the second component eluted from the column was deprotected by heating in 3 N sodium hydroxide solution at 80°–90° C. for 4 hours. Neutralization and purification by ion exchange chromatography on Amberlite CG-50 (ammonium-ion form), eluting as before gave 1-N-[1-(hydroxymethyl)-2-hydroxyethyl]kanamycin A identical with the product of Example 18.

EXAMPLE 25

The procedure of Example 1 is repeated, except that the 3,3″,6′-tri-N-formylkanamycin A is replaced by 6′-N-methyl-3,3″,6′-tri-N-formylkanamycin A, 6′-N-ethyl-3,3″,6′-tri-N-formylkanamycin A and 6′-N-butyl 3,3″,6′-tri-N-formylkanamycin A, respectively. This affords:

6'-N-methyl-1-N-[(S)2,3-dihydroxypropyl]kanamycin A,
6'-N-ethyl-1-N-[(S)2,3-dihydroxypropyl]kanamycin A and
6'-N-butyl-1-N-[(S)2,3-dihydroxypropyl]kanamycin A, respectively.

EXAMPLE 26

The procedure of Example 19 is repeated, except that the 2',3,3'',6'-tetra-N-formylkanamycin B is replaced by 6'-N-methyl-2',3,3'',6'-tetra-N-formylkanamycin B and 6'-N-butyl-2',3,3'',6'-tetra-N-formylkanamycin B, respectively. This affords:
6'-N-methyl-1-N-[1-(hydroxymethyl)-2-hydroxyethyl]kanamycin B and
6'-N-butyl-1-N-[1-(hydroxymethyl)-2-hydroxyethyl]kanamycin B,
respectively.

EXAMPLE 27

1-N-[1-(Hydroxymethyl)-2-hydroxyethyl]tobramycin

The title compound is prepared by replacing the hydroxyacetone of Example 22 by dihydroxyacetone.

EXAMPLE 28

Results of the testing of the compounds of the Examples for antibacterial activity in vitro by the methods previously described are given in the following Table:

| Example No. | E. Coli | Klebsiella pneumoniae | Proteus mirabilis | Pseudomonas aeruginosa | Staphylococcus aureus |
|---|---|---|---|---|---|
| 1 | 6.2 | 6.2 | 25 | 6.2 | 6.2 |
| 2 | 12.5 | 6.2 | 12.5 | 6.2 | 6.2 |
| 3 | 12.5 | 12.5 | 12.5 | 6.2 | 6.2 |
| 4 | 12.5 | 12.5 | 25 | 12.5 | 12.5 |
| 5 | 12.5 | 12.5 | 25 | 12.5 | 12.5 |
| 6 | 25 | 25 | 50 | 25 | 25 |
| 7 | 12.5 | 12.5 | 25 | 12.5 | 6.2 |
| 8 | 50 | 25 | 100 | 25 | 25 |
| 9 | 25 | 12.5 | 25 | 12.5 | 25 |
| 10 | 25 | 25 | 100 | 25 | 25 |
| 11 | 6.2 | 3.1 | 6.2 | 3.1 | 1.6 |
| 12 | 3.1 | 3.1 | 6.2 | 1.6 | 1.6 |
| 13 | 3.1 | 3.1 | 12.5 | 3.1 | 1.6 |
| 14 | 3.1 | 3.1 | 6.2 | 3.1 | 1.6 |
| 15 | 6.2 | 6.2 | 100 | 6.2 | 6.2 |
| 16 | 6.2 | 3.1 | 12.5 | 3.1 | 3.1 |
| 17 | 6.2 | 6.2 | 12.5 | 6.2 | 3.1 |
| 18 | 6.2 | 6.2 | 25 | 3.1 | 6.2 |
| 19 | 3.1 | 1.6 | 6.2 | 1.6 | 1.6 |
| 20 | 3.1 | 3.1 | 25 | 3.1 | 1.6 |
| 21 | 3.1 | 3.1 | 12.5 | 6.2 | 3.1 |
| 22 | 3.1 | 6.5 | 12.5 | 3.1 | 0.8 |
| 23 | 6.2 | 3.1 | 6.2 | 3.1 | 1.6 |

EXAMPLE 29

1-N-[1-(Hydroxymethyl)-2-hydroxyethyl]kanamycin B

A. Sodium cyanoborohydride (6.24 g.) was added to a solution of 2',3,3'',6'-tetra-N-formyl-kanamycin B (18.0 g.) and dihydroxyacetone (8.17 g.) in dimethylsulfoxide (900 ml.). 2 N Hydrochloric acid (3.6 ml.) was added and the solution was heated at 60°–70° C. for 5 hours. The solvent was removed under high vacuum, and the crude product was dissolved in water. The aqueous soution was acidified to pH 5.3 with 6 N hydrochloric acid, and the resulting solution was chromatographed on a column of Sephadex CM25 ion-exchange cellulose (ammonium ion form) eluting with water and 0.005 N aqueous ammonium hydroxide. Fractions containing the desired 1-N-[1-(hydroxymethyl)-2-hydroxyethyl]2',3,3'',6'-tetra-N-formyl-kanamycin B were combined and evaporated (yield 13.7 g., 68%).

B. 1-N-[1-(Hydroxymethyl)-2-hydroxyethyl]-2',3,3'',6'-tetra-N-formyl-kanamycin B (4.69 g.) was dissolved in 1N aqueous sodium hydroxide (141 ml.) and the solution was warmed at 55°–60° C. for 3.5 hours. The solution was cooled, acidified to pH 5.5 with 6 N hydrochloric acid and then the product was chromatographed on a column of Sephadex CM25 ion-exchange cellulose (ammonium ion form) eluting with water and with ammonium hydroxide of increasing concentrations. Fractions containing the product were combined and evaporated to yield 1-N-[1-(hydroxymethyl)-2-hydroxyethyl]kanamycin B (2.42 g., 62%) identified by comparison with the product of Example 19.

PREPARATION A

3'',6'-Di-N-acetylkanamycin A (A) A solution of 1,3,3'',6'-tetra-N-benzyloxycarbonyl kanamycin A (*Bull.* Chem. Soc. Japan, 38, 1181 [1965]) (189.4 g.) in pyridine (568 ml.) and acetic anhydride (189 ml.) was stirred overnight at room temperature and then poured into water (1.9 liters). The aqueous solution was extracted with chloroform (1×1.8 liters and 1×1.0 liters) and the organic extract was evaporated to dryness under reduced pressure. Trituration of the residue with ether gave penta-O-acetyl-1,3,3'',6'-tetra-N-benzyloxycarbonyl kanamycin A (224.8 g.) which was filtered and dried under vacuum. The product had m.p. 223°–229°; Rf 0.55 in chloroform-ethanol (12:1), δ 1.8–2.05 (15 proton multiplet, 5 acetyl groups) and 7.4 (20 proton singlet, 4 phenyl groups).

(B) A solution of penta-O-acetyl-1,3,3'',6'-tetra-N-benzyloxycarbonyl kanamycin A (53 g.) in ethyl acetate (260 ml.) containing glacial acetic acid (260 ml.) was hydrogenated over 5% palladium on carbon (15 g.) at 60° and 50 p.s.i. for 7 hours. The solution was filtered and the filtrate was evaporated to dryness under reduced pressure. The residue was triturated with ether and the product penta-O-acetylkanamycin (32.9 g.) was collected and dried under vacuum, m.p. 97°–105°, Rf 0.0 in chloroform, ethanol (12:1) compared to an Rf of 0.55 for the starting material. The proton magnetic resonance spectrum showed a complete absence of aromatic protons.

(C) A solution of penta-O-acetyl kanamycin A (139.2 g.) in methanol (1.4 liters) saturated with ammonia was allowed to stand overnight at room temperature and then evaporated to dryness under reduced pressure. The residue was dissolved in methanol (140 ml.) and the crude product was precipitated with chloroform (2.5 liters), filtered and dried in vacuum. The crude solid was slurried with ethanol (400 ml.) and the 3'',6'-di-N-acetylkanamycin A (91.9 g.) was collected by filtration, washed with ether and dried under vacuum, m.p. 150°–180°, Rf 0.77 in methanol-0.880 ammonium hydroxide (1:1). It gave a $^{13}C$ n.m.r. spectrum and proton n.m.r. spectrum in full agreement with the required structure.

PREPARATION B

2',3'',6'-Tri-N-triflfuoroacetylkanamycin B

Trifluoroacetic anhydride (3.6 ml.) was added slowly to a stirred solution of kanamycin B (960 mg., 2 mmole) in trifluoroacetic acid (50 ml.) at 0°. The solution was allowed to stand at 0°–4° for 20 hours. The solvent was then evaporated under reduced pressure and the residue treated with toluene (10 ml.) and evaporated to dryness. The trifluoroacetate salt was dissolved in tetrahydrofuran (30 ml.) and added slowly to a stirred solution of excess triethtylamine in tetrahydrofuran. The solution was allowed to stand at room temperature for 40 minutes and the solvent was then evaporated under reduced pressure. The residue was dissolved in methanol to hydrolyze the remaining O-trifluoroacetyl groups and after 30 minutes at room temperature the solvent was evaporated under reduced pressure and the product was chromatographed on silica eluting with a solvent gradient of chloroform-methanol (3:1) to chloroform-methanol-17% ammonium hydroxide (20:10:1) to give 2',3",6'-tri-N-trifluoroacetyl-kanamycin B (452 mg., 29%) as a glass. Rf 0.70 in methanol-chloroform-8% ammonium hydroxide 4:1:0.1 (kanamycin B gave an Rf of 0.0).

The structure was confirmed by the following sequence of reactions:

(a) acetylation with acetic anhydride in methanol for 20 hours at room temperature followed by treatment with 1 N ammonium hydroxide for 18 hours to remove the trifluoroacetyl groups gave a product containing two acetyl groups. m/e (field desorption) found 568, $C_{22}H_{41}N_5O_{12}$ requires M+1 568; (b) Treatment pf this product with deuterioacetic anhydride in methanol at room temperature for 24 hours followed by reaction with a 2:1 mixture of hexamethyldisilazane and trimethylchlorosilane at room temperature for 24 hours gave the volatile tri-N-deuteroacetyl-di-N-acetyl-hexa-O-trimethylsilyl derivative. m/e found 1134, $C_{46}H_{86}N_5O_{15}D_9Si_6$ requires m/e 1134. Diacetylation was shown to have occurred on the 2-deoxystreptamine ring from the fragmentation pattern, thereby confirming that trifluoroacetylation had initially taken place on the 2',3" and 6' positions in kanamycin B.

PREPARATION C

3",6'-Di-N-trifluoroacetylkanamycin A

Trifluoroacetic anhydride (5.0 ml.) was added slowly to a stirred solution of kanamycin A (1.0 g.) in trifluoroacetic acid (40 ml.) at 0°. The solution as allowed to stand at 0°–4° for 20 hours. The solvent was then evaporated under vacuum and the residue was treated with toluene (10 ml.) and evaporated to dryness. The trifluoroacetate salt was dissolved in dry tetrahydrofuran and neutralized by slowly adding to a stirred suspension of excess anhydrous potassium carbonate in tetrahydrofuran. The mixture was stirred at room temperature for 20 minutes and the suspension was then filtered and the filtrate evaporated to dryness. The product was dissolved in methanol (20 ml. and kept at room temperature for 30 minutes. The solvent was evaporated under reduced pressure and the residue was chromatographed on silica, eluting with a solvent gradient of chloroform-methanol (3:1) to chloroform-methanol-17% ammonium hydroxide (8:4:1) to give 3",6'-di-N-trifluoroacetylkanamycin A hydrate (0.52 g.) as a white hygroscopic solid. Rf 0.7 in methanol, chloroform, 17% ammonium hydroxide 4:1:1 (kanamycin A gave an Rf of 0.05). $\nu$ c=o 1665 cm$^{-1}$.

A sample was converted to the volatile di-N-acetyl-hepta-O-trimethysilyl derivative as described in Preparation F. m/e found 1264. $C_{47}H_{94}N_4O_{15}F_6Si_7$ requires m/e 1264.

PREPARATION D

3-N-Benzyl-3",6'-di-N-trifluoroacetylkanamycin A

Trifluoroacetic anhydride (0.7 ml., 5 mmole) was added slowly to a solution of 3-N-benzylkanamycin A (0.23 g., 0.4 mmole) in trifluoroacetic acid (15 ml.) at 0°. The solution was kept at 0°–4° for 20 hours. The solvent was then evaporated and the residue treated with toluene (10 ml). and evaporated to dryness. The product was dissolved in tetrahydrofuran (20 ml.) and slowly added to a stirred suspension of excess potassium carbonate in tetrahydrofuran. The suspension was stirred at room temperature for 30 minutes, filtered and the filtrate evaporated to dryness under reduced pressure. The residue was dissolved in methanol (20 ml.) and allowed to stand at room temperature for 30 minutes. The solvent was then removed under vacuum to yield 3-N-benzyl-3",6'-di-N-trifluroacetylkanamycin A Rf 0.5 in methanol-chloroform-8% ammonium hydroxide, 4:1:0.1 (3-N-benzylkanamycin A gave an Rf value of 0.01).

PREPARATION E

3-N-Benzylkanamycin A

Kanamycin A sulphate (24.3 g., 0.03 mole) was dissolved in water (150 ml.) and the pH adjusted to 6 by the dropwise addition of 5 N hydrochloric acid. Sodium cyanoborohydride (1.95 g., 0.03 mole) was added and the mixture was cooled to 0° C. and stirred while a solution of benzaldehyde (3.61 g., 0.033 mole) dissolved in methanol (15 ml.) was added slowly over the course of 2½ hours. The mixture was allowed to warm to room temperature. After 16 hours the pH of the solution was adjusted to 5.5 by the addition of 1 N hydrochloric acid and the solution was filtered and added to a column of Amberlite CG-50 ion-exchange resin in the ammonium-ion form. Elution first with water and then with a gradient of ammonium hydroxide of increasing concentration from 0–0.7 N gave as major product 3-N-benzylkanamycin A contaminated with some 1-N-benzyl derivative (5.0 g., 28%) Rf 0.44 in methanol-chloroform-17% ammonium hydroxide 4:1:2. (Kanamycin A gave an Rf value of 0.15).

A sample was converted to the volatile tetra-N-acetyl-hepta-O-trimethylsilyl derivative by treatment with acetic anhydride in methanol at room temperature for 24 hours followed by reaction with a 2:1 mixture of hexamethyldisilazane and trimethylchlorosilane at room temperature for 24 hours. m/e found 1246. $C_{54}H_{106}N_4O_{15}Si_7$ requires m/e 1246.

The position of substitution was confirmed by the following sequence of reactions: (a) treatment with t-butyloxycarbonyl azide gave a compound containing three t-butyloxycarbonyl groups as well as the benzyl group (from n.m.r (b) hydrogenation to remove the benzyl group, (c) acylation with N-[(S)-4-benzyloxycarbonylamino-2-hydroxy-butyryloxy]succinimide, and (d) removal of the N-protecting groups by hydrogenation followed by treatment with trifluoroacetic acid gave, as major product, 3-N-[(S)-4-amino-2-hydroxybutyryl]kanamycin A (BB-K29) identified by comparison with an authentic sample prepared according to the procedure of Naito et al., Journal of *Antibiotics*, 26, 297 (1973).

What is claimed is:
1. A compound of the formula

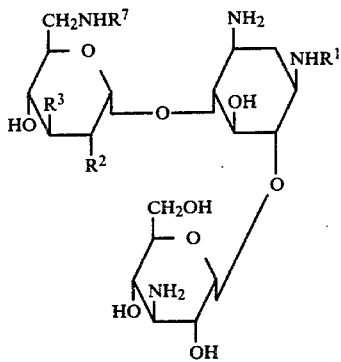

and the pharmaceutically-acceptable acid addition salts thereof; wherein

R$^2$ is selected from the group consisting of hydroxy and amino;

R$^3$ is selected from the group consisting of hydrogen and hydroxy;

R$^7$ is selected from the group consisting of hydrogen and alkyl having from 1 to 4 carbon atoms; and R$^1$ is selected from the group consisting of

CH$_2$—R$^8$ and

wherein

R$^8$ is alkyl having from 2 to 5 carbon atoms at least 2 of which bear one hydroxy group;

R$^9$ is alkyl having from 1 to 5 carbon atoms at least one of which bears one hydroxy group; and R$^{10}$ is alkyl having from 1 to 5 carbon atoms at least one of which bears one hydroxy group.

2. A compound according to claim 1, wherein R$^1$ is CH$_2$-R$^8$.

3. A compound according to claim 2, wherein R$^3$ is hydroxy.

4. A compound according to claim 3, wherein R$^7$ is hydrogen.

5. A compound according to claim 4, wherein R$^8$ is a straight-chain alkyl group having from 2 to 5 carbon atoms each of which bears one hydroxy group.

6. A compound according to claim 5, wherein R$^8$ is 1,2-dihydroxyethyl.

7. The compound according to claim 6, wherein R$^2$ is hydroxy.

8. The compound according to claim 6, wherein R$^2$ is amino.

9. A compound according to claim 2, wherein R$^2$ is amino and R$^3$ and R$^7$ are each hydrogen.

10. A compound according to claim 9, wherein R$^8$ is a straight-chain alkyl group having from two to five carbon atoms each of which bears one hydroxy group.

11. The compound according to claim 10, wherein R$^8$ is 1,2-dihydroxyethyl.

12. A compound according to claim 1, wherein R$^1$ is

13. A compound according to claim 12, wherein R$^3$ is hydroxy.

14. A compound according to claim 13, wherein R$^7$ is hydrogen.

15. A compound according to claim 14, wherein R$^9$ and R$^{10}$ are each straight-chain alkyl having from one to five carbon atoms each of which bears one hydroxy group.

16. A compound according to claim 15, wherein R$^9$ and R$^{10}$ are each hydroxymethyl.

17. The compound according to claim 16, wherein R$^2$ is hydroxy.

18. The compound according to claim 16, wherein R$^2$ is amino.

19. A compound according to claim 12, wherein R$^2$ is amino, R$^3$ and R$^7$ are each hydrogen, and R$^9$ and R$^{10}$ are each hydroxymethyl.

* * * * *